United States Patent [19]

Crombie

[11] 4,306,023

[45] Dec. 15, 1981

[54] PRODUCTION OF ALCOHOL

[75] Inventor: Lance B. Crombie, Webster, Minn.

[73] Assignee: Robert S. Butler, St. Paul, Minn.

[21] Appl. No.: 118,433

[22] Filed: Feb. 4, 1980

[51] Int. Cl.³ .......................... C12P 7/06; C12C 1/00; C12M 1/04
[52] U.S. Cl. ...................................... 435/161; 435/93; 435/313
[58] Field of Search ................ 435/161, 93, 813, 313; 426/18, 21, 60, 626, 14, 519, 520, 29; 127/37, 38

[56] References Cited

U.S. PATENT DOCUMENTS

| | | | |
|---|---|---|---|
| 963,275 | 7/1910 | Chute | 435/161 |
| 2,086,701 | 7/1937 | Dreyfus | 127/37 |
| 3,169,083 | 2/1965 | Taylor | 127/38 |
| 3,405,920 | 10/1968 | Lefrancois | 435/313 |
| 4,092,434 | 5/1978 | Yoshizumi et al. | 435/93 |

FOREIGN PATENT DOCUMENTS

497298 10/1953 Canada .............................. 435/161

OTHER PUBLICATIONS

Underkofler, L. A. & Hickey, R. J. Eds., *Industrial Fermentations*, vol. I, 1954, Chemical Publishing Co., Inc., pp. 51 and 52.

Kirk, R. E. & Othmer, D. F. Eds., *Encyclopedia of Chemical Technology*, First Edition, vol. 12, p. 765.

*Primary Examiner*—Alvin E. Tanenholtz
*Assistant Examiner*—Elizabeth J. Curtin
*Attorney, Agent, or Firm*—Dressler, Goldsmith, Shore, Sutker & Milnamow, Ltd.

[57] ABSTRACT

A process of producing ethyl alcohol is disclosed in which the wort is formed by separately supplying to a fermentation tank (1) a moist particulate feed containing a component convertible to a fermentable sugar under pressure and at a temperature in excess of about 250° F. (preferably using an auger feed having a restrictive outlet) which induces rapid conversion to fermentable sugar before the feed enters the wort, and (2) an aqueous liquor which mixes with the converted feed to form the wort which contains yeast or other microorganism for converting the fermentable sugar to ethyl alcohol. The firmentation process is desirably carried out continuously, a portion of the wort being continuously or periodically removed, and the solids removed therefrom to provide a beer which is distilled to remove alcohol and provide a sugar-containing aqueous liquor which is recycled to the fermentation tank. The wort is preferably agitated by mixing air with the carbon dioxide gas exiting the tank and bubbling the mixture through the wort.

12 Claims, 1 Drawing Figure

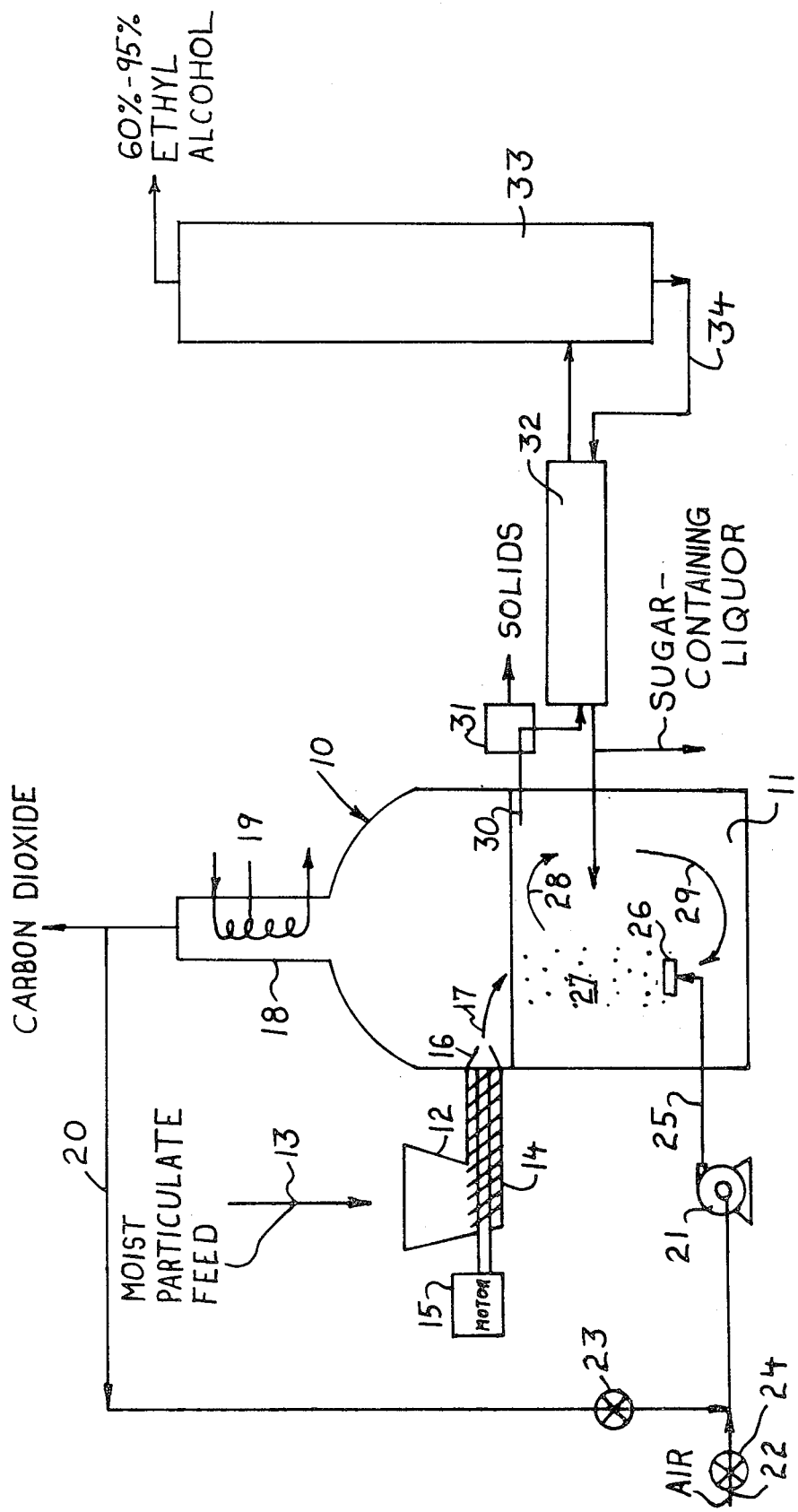

PRODUCTION OF ALCOHOL

DESCRIPTION

1. Technical Field

This invention relates to the production of ethyl alcohol, particularly to provide a combustible liquid fuel.

2. Background Art

Fermentation to produce ethyl alcohol is itself well known, but the existing processes require large amounts of heat and are slow and cumbersome such that, even using complex equipment to maximize efficiency, it is questionable as to whether the energy which can be obtained by combustion of the alcohol product will exceed the energy needed to produce and distill the alcohol. This invention includes many features, the overall thrust of which is to simplify the needed construction and operation, to enable continuity of operation, and to minimize the energy needed to produce the alcohol.

DISCLOSURE OF THE INVENTION

As one feature of this invention, a moist finely divided feed containing a component convertible to a fermentable sugar is supplied to a fermentation tank under pressure and at high temperature while most of the water or other aqueous liquor to be used in the fermentation process is separately supplied. Starch is the usual component which is convertible to a fermentable sugar, but cellulose and other sugars are also contemplated. The temperature and the optional presence of acid catalyst are selected to cause rapid conversion to fermentable sugar. In this way, only a small proportion of the fermentation liquor, usually termed the wort, has to be heated. As an illustration, and using an auger feed with a restricted outlet, the energy of compressing and feeding the moist particulate feed can produce a temperature of about 350° F. which will provide the desired sterilization of the feed and conversion of starch in ground corn to fermentable sugars in about 7 to 10 seconds.

This rapid conversion of starch, cellulose or sugars to fermentable sugars by heating only a moist particulate feed minimizes the energy input because there is no need to heat the entire liquid contents of a dilute aqueous suspension, as is present in the wort which is fermented.

The presence of a small amount of acid in the feed is helpful, in some instances, to minimize the temperature and time requirements Fermentation requires that the wort be maintained at an elevated temperature, the exact temperature which is selected being a function of the yeast or other microrganism used in the process. This heat is supplied in part by the heating of the moist feed, and in part by the exothermic fermentation process. If the temperature tends to become excessive, it can be limited by increasing the ratio of aqueous liquor to fermentable material or by increasing the amount of fresh cold water in the aqueous liquor supplied to the fermentation tank. By reducing the ratio or porportion, the temperature can be increased. Extraneous heating or cooling may be used, when these are available, but the need therefor is minimized in this invention.

The fermentation process in this invention is preferably conducted on a continuous basis. Continuous processing has the obvious advantage that the yeast in the fermentation tank constantly regenerate themselves, so once the fermentation process is started, there is no need to add yeast or other microorganisms to the process.

Continuous fermentation in an effective manner is not simple. Heuser U.S. Pat. No. 1,302,549 suggests simultaneously boiling and fermenting the wort in a vacuum at yeast fermentation temperature, but this is not a practicable procedure. Instead, and as a feature of this invention, the fermentation process is carried out in a fermentation tank which is agitated to maintain a relatively uniform composition throughout the tank, and a small portion of the contents of the tank is continuously or periodically withdrawn, the solids portion is removed, and the resulting "beer" is distilled to remove the alcohol and provide an aqueous liquor which contains fermentable sugars and other dissolved materials. A portion of this sugar-containing liquor is recycled to the fermentation tank, and the balance is used in diverse ways.

It should be noted that the removed solids are rich in protein when the feed is proteinaceous, as when the feed is ground corn. These removed solids provide an excellent animal feed which may be wet or dry, as desired. The wet solids obtained by filtration or centrifuging can be spread in large trays to dry in the sun, and the unrecycled balance of the aqueous beer can be poured over the solids to enhance the sugar and salt content of the proteinaceous solids.

The agitation requirement of the continuous fermentation process can be satisfied with any type of agitation, As another feature of this invention, air is combined with the carbon dioxide gas exiting from the fermentation tank, and this gas mixture (or a portion thereof) is supplied to a diffuser positioned in the tank to create a rising column of gas-containing wort which causes a circulation of the contents of the tank, and thus provides the desired agitation without a mechanical agitator.

The air-carbon dioxide mixture is itself significant because air itself contains too much oxygen. By adjusting the ratio of air to gas exiting the fermentation tank, one can make sure that the proportion of oxygen is correct. Without added oxygen, the fermentation produces too much carbon dioxide to permit it to be recycled. With too much oxygen, the fermentation is slowed and the yield of alcohol is decreased.

While the beer may be distilled in conventional fashion, solar distillation is particularly desirable since, in the absence of sophisticated distillation equipment, the energy required for distillation can be excessive. The details of the distillation process form no part of this invention.

Conventional distillation, as is well known, produces an alcohol concentrate which may contain up to about 95% by weight of alcohol, the balance being water forming an azeotropic boiling mixture with the alcohol which resists further separation by distillation. Another feature of this invention is to use a water-absorbing starch powder, such as ground corn, to remove the water which remains in the distillate. The starch absorbs water without absorbing alcohol, and the water moistens the finely divided feed so that it is pasty and appropriate for screw feeding. Correlating the ground corn used as feed with the water in the alcohol product, the ground corn can remove the water from the alcohol when it contains as much as 40% water. It is easier to produce alcohol of 60% to 70% concentration and to use the dry corn feed to remove the remaining water to provide the moist feed needed in this invention.

The moist feed should have a moisture content of at least about 20% by weight, but the amount of water should be small enough that the water does not provide a continuous aqueous phase in the particulate feed. In this way, the moist feed can be compressed by a screw feed and the pressure of the screw can be used to rapidly heat the feed. While it is not needed, the auger can be separately heated to further increase temperature, or to speed the rate at which fresh feed is supplied to the fermentation tank.

The moist feed is heated to a temperature of at least about 250° F., preferably at least about 300° F. So long as the liquid phase is maintained, there is no maximum temperature. 300° F. to about 450° F. represents preferred conditions which are maintained for from 5 seconds to 30 seconds.

BRIEF DESCRIPTION OF DRAWINGS

The process of this invention is illustrated in the accompanying drawing which shows the process in diagramatic form.

BEST MODE FOR CARRYING OUT THE INVENTION

Referring more particularly to the drawing, the numeral 10 identifies a fermentation tank wherein the wort 11 is confined. The wort is itself conventional in that it is a dilute aqueous liquor containing a mash of fermentable sugar-containing material suspended in water. The sugars, of course, dissolve in the water phase of the liquor. This liquor contains a yeast or other microorganism for converting the fermentable sugars to ethyl alcohol, all of which is conventional, and the wort is maintained at a temperature conducive to fermentation, e.g., about 90° F. to 140° F.

A feed in the form of finely ground corn which has been moistened so as to be damp, preferably by having been used to dry previously produced 60% to 70% ethyl alcohol, is supplied to the process via hopper 12 as shown by arrow 13. The hopper 12 communicates at its lower end with an auger feed 14 which is powered by motor 15. The auger 14 terminates within the tank 11 and has a restricted orifice 16 so that heat and pressure are established within the auger causing conversion of starch to fermentable sugar. The hot pasty mixture produced in the auger 14 is sprayed into tank 10 as indicated by arrow 17.

Fermentation within the tank 10 produces carbon dioxide which exits from the tank via column 18 which may contain cooling coils to remove heat from the system as indicated at 19 and to condense alcohol which drops back into the tank.

A portion of the carbon dioxide is removed via line 20 by means of pump 21 and air is also drawn in via line 22, the relative proportions of each being controlled by valves 23 and 24 so that carbon dioxide production is minimized and the fermentation rate is maximized.

The mixture of air and carbon dioxide is passed via line 25 to a diffuser 26 and the bubbles released by the diffuser form a rising column of liquor 27 which agitates the contents of the tank as indicated by circulation arrows 28 and 29.

A portion of the wort 11 is removed, and this is conveniently accomplished using an overflow line 30. This wort contains solids which are removed in a centrifuge 31 and the beer so-provided is passed via heat exchanger 32 to a distillation column indicated diagramatically at 33. The product of this distillation column is 60% to 95% ethyl alcohol which is removed overhead, and the sugar-containing liquor which is formed when the alcohol is removed is withdrawn at the bottom via line 34. The liquor in line 34 is hot and much of it is recycled to the tank 10 after passing through heat exchanger 32 to preheat the liquor moving into the distillation column 33. The distillation may be carried out at atmospheric pressure or under vacuum as desired.

The acid used to enhance conversion to fermentable sugars may be acetic acid, and it can be mixed in with the feed.

The specific form of distillation used is not material to this invention.

What is claimed is:

1. A process of producing ethyl alcohol comprising separately supplying to a wort within a fermentation tank:
   (1) a moist particulate feed containing a component convertible to a fermentable sugar and including at least about 20% by weight of water, but insufficient water to provide a continuous aqueous phase in the particulate feed, said moist feed being sprayed into said fermentation tank by means of an auger feed with a restricted outlet, in which said moist feed is under pressure and at a temperature in excess of about 250° F. and under conditions which induce rapid conversion to fermentable sugar before spraying the feed; and
   (2) an aqueous liquor which mixes with the converted feed and is added to said wort; said wort containing yeast or other microorganism for converting said fermentable sugar to ethyl alcohol, said wort being maintained at an elevated temperature at which said yeast or other microorganism can reproduce and convert said fermentable sugar to ethyl alcohol as part of their life processes, and agitating said wort.

2. A process as recited in claim 1 in which the process is carried out continuously, a portion of the wort being continuously or periodically removed from said fermentation tank, removing solids from the portion of the wort which is removed to provide a beer, and distilling said beer to remove alcohol and provide a sugar-containing aqueous liquor.

3. A process as recited in claim 2 in which said sugar-containing aqueous liquor is recycled to said fermentation tank to provide a portion of the aqueous liquor used in component (2).

4. A process as recited in claim 1 in which said moist particulate feed contains starch and is heated to a temperature of at least about 350° F. for a period of at least 7 to 10 seconds.

5. A process as recited in claim 4 in which said moist feed is ground corn.

6. A process as recited in claim 1 in which said moist feed contains added acid to lower its pH and thereby minimize the time and temperature needed to produce fermentable sugars and to enhance fermentation conditions.

7. A process as recited in claim 3 in which the temperature of the wort is prevented from becoming excessive by increasing the ratio of aqueous liquor to feed or by increasing the amount of fresh cold water in the aqueous liquid supplied to said fermentation tank.

8. A process as recited in claim 1 in which a mixture of air and carbon dioxide gas exiting said tank are bubbled through the wort to agitate the same and to maximize the fermentation process.

9. A process as recited in claim 1 in which said beer is distilled to provide about 60–95% ethyl alcohol, and the moist feed is formed by contacting finely divided starch with the said alcohol to remove water therefrom.

10. A process as recited in claim 9 in which said beer is distilled to provide ethyl alcohol of 60% to 70% concentration.

11. A process as recited in claim 1 in which yeast is employed which propagates at about 90° F. to 140° F., and said wort is maintained at about 90° F. to 140° F.

12. A process as recited in claim 1 in which said moist feed is maintained at a temperature of about 300° F. to about 450° F. and is sprayed into said wort.

* * * * *